United States Patent [19]

Neumann et al.

[11] 4,343,897
[45] Aug. 10, 1982

[54] REAGENT FOR THE DETERMINATION OF LIPASE AND PROCESS FOR PREPARING SAME

[75] Inventors: Ulrich Neumann, Peissenberg; Karl-Wolfgang Knitsch, Andechs; Joachim Ziegenhorn, Starnberg; Albert Röder; Werner Zwez, both of Seeshaupt; Werner Krämer, Bernried, all of Fed. Rep. of Germany

[73] Assignee: Boehringer Mannheim GmbH, Mannheim-Waldhof, Fed. Rep. of Germany

[21] Appl. No.: 115,864

[22] Filed: Jan. 28, 1980

[30] Foreign Application Priority Data

Feb. 5, 1979 [DE] Fed. Rep. of Germany ....... 2904305

[51] Int. Cl.$^3$ .............................................. C12Q 1/44
[52] U.S. Cl. ...................................... 435/19; 252/312; 252/314; 252/408

[58] Field of Search .................. 252/312, 408; 435/12, 435/19

[56] References Cited

U.S. PATENT DOCUMENTS 3,527,674  9/1970  Deutsch ................................. 435/12
3,898,130  8/1975  Komatsu ........................... 435/19 X
3,917,515  11/1975  Goldberg ............................... 435/19
4,115,313  9/1978  Lyon et al. ...................... 252/312 X Primary Examiner—Richard D. Lovering
Attorney, Agent, or Firm—Felfe & Lynch

[57] ABSTRACT

A reconstitutable dry reagent for the turbidimetric determination of lipase, which reagent forms an emulsion upon adding water and comprises substrate oil, protective colloid, emulsifier and activator; and the process for making said dry reagent comprising preparing an aqueous emulsion of a triglyceride containing bile acid salt, colipase, at least 10% by weight of protective colloid, and at least a part of a preserving agent, lyophilizing the emulsion, mixing the lyophilizate with a buffer substance and urea, and recovering said dry reagent.

18 Claims, 4 Drawing Figures

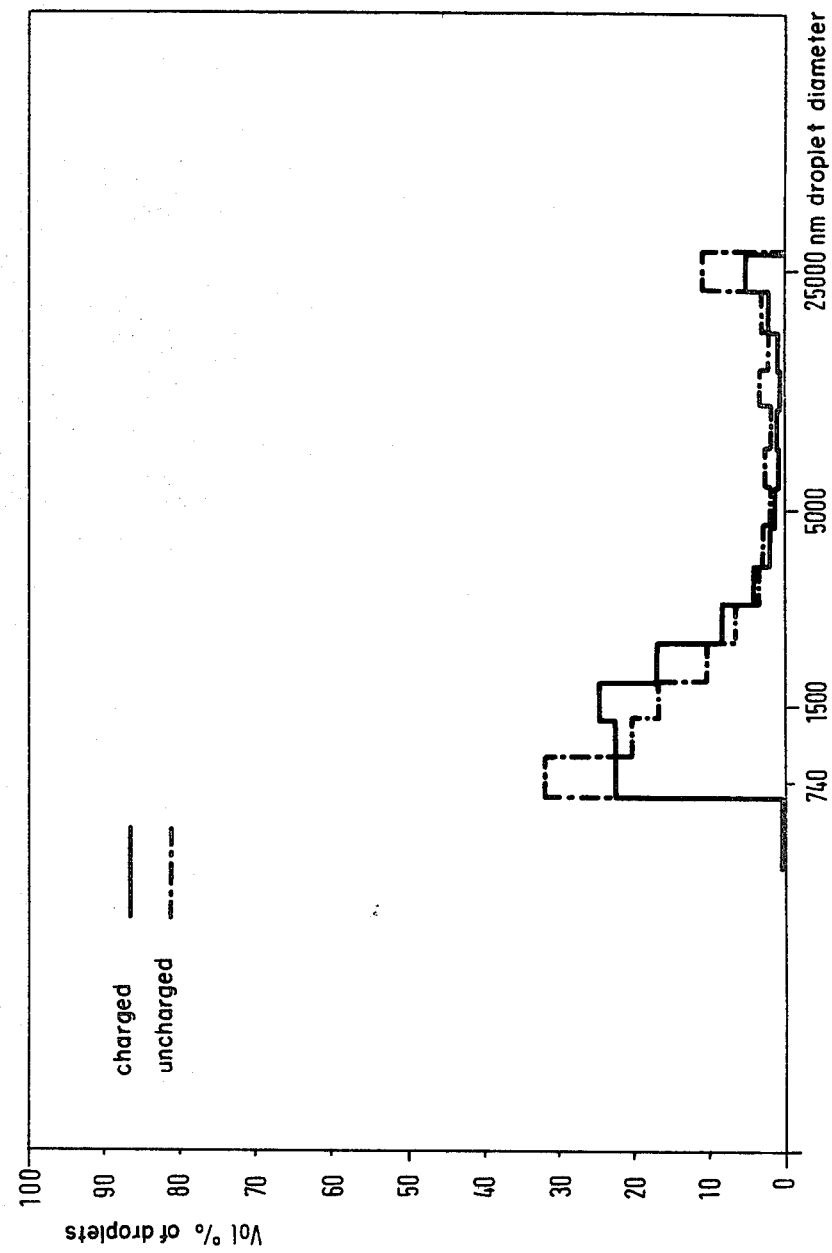

REAGENT FOR THE DETERMINATION OF LIPASE AND PROCESS FOR PREPARING SAME

This invention relates to a reagent for the determination of lipase and with the manufacture thereof. More specifically, the invention relates to a reagent for the turbidimetric determination of lipase.

For the diagnosis of pancreatic disease, the determination of the enzymes amylase (E.C. 3.2.1.1) and lipase (E.C. 3.1.1.3) is of great significance. In the case of acute pancreatitis, within the course of a few hours there is, inter alia, a very massive increase of both of these enzymes in the serum. However, when kidney function is unimpaired, the amylase, because of its low molecular weight is rapidly excreted again, whereas the lipase activity in the serum remains high for quite a long time. An accurate diagnosis of pancreatitis is obtained by determination of both enzymes.

Lipase primarily splits the $\alpha$-ester bond of a triglyceride with preferably long-chained fatty acid residues to give a diglyceride and free fatty acid. Further reaction to give a monoglyceride takes place much more slowly.

Whereas the usual reactions catalyzed by enzymes take place in aqueous phase, lipase only acts on the boundary surface of oil droplets/water. In this way, it differs from the esterases which react in the aqueous phase. Therefore, besides the chemical parameters, the kinetics of the reaction are influenced to a large extent by the properties of the surface of the substrate.

Titrimetric methods for the determination of lipase are known. However, because of, in some cases, the difficult handling, long periods of reaction and the large samples required, such methods have only found limited use in the routine clinical-chemical laboratory.

The substantial disadvantages of the titrimetric methods of determination, namely, the large samples required and the long incubation times, are avoided in the case of turbidimetric methods in which clarification of the turbidity of a triglyceride/water emulsion is followed photometrically. However, a considerable problem in the case of turbidimetric determinations is the production of an emulsion which can always be depended upon to have the same droplet size. This is of especial importance since the kinetics of the reaction are very considerably influenced by the size of the triglyceride droplets. Federal Republic of Germany published patent application No. 19 61 983 discloses an olive oil dry emulsion which can be used for the titrimetric determination of lipase activity. However, in the case of this dry emulsion, the triglyceride content is not suitable for a photometric determination of the clarification of turbidity because of the high light absorption. If this reagent is diluted with the object also of making it suitable for a turbidimetric kinetic lipase determination, the parameters are, however, displaced in such a manner that a reaction of zeroth order is no longer obtained.

Therefore, it is an object of the present invention to provide a reagent which is particularly suitable for the turbidimetric or nephelometric determination of the activity of lipase, which is present in dry form and which, by simply mixing with water, can be converted into an emulsion with reproducably uniform droplet size.

A further object of the present invention is to provide a reagent of this kind in the case of which the droplet size of the reconstituted emulsion can be regulated by the quantitative composition of the dry reagent and is substantially independent of the triglyceride emulsion used for the production of the dry reagent. Thus, it is to be possible for the user to be able to avoid having to produce the triglyceride emulsion immediately before carrying out a test. Since, however, the properties of the substrate surface determine, to a large extent, the activity of the enzyme (see Clin. Chem., 23, 522–553/1977), in order to be able to obtain dependable results, it is necessary always to have a uniform substrate surface, also with regard to the droplet size. However, the quality of the emulsion is very largely dependent upon the production technique used and, as is known from experience, even when maintaining definite procedures, in the case of carrying out by different persons, considerable deviations in the measured activity values occur. This difficulty is also to be overcome by the present invention.

Thus, according to the present invention, there is provided a reconstitutable dry reagent especially for the turbidimetric determination of lipase, which reagent forms an emulsion upon adding water and comprises substrate oil, protective colloid, emulsifier and activator, said reagent containing:

0.2 to 10% by weight of liquid triglyceride,
20 to 90% by weight of protective colloid,
5 to 60% by weight of an alkali metal salt of a bile acid,
0.001 to 0.1% by weight of colipase,
0.1 to 2.0% by weight of preserving agent,
if desired, 5 to 20% by weight of urea,
3 to 50% by weight of buffer substance for pH 6.0 to 10.5 and,
0.5 to 5% by weight of activator.

Surprisingly, we have found that, in the case of the composition according to the present invention, a dry reagent is obtained, in the case of constant quantitative composition, which always dependably gives the same droplet size in the reconstituted emulsion and, furthermore, the properties of the substrate surface are reproducably so characterised that there is always achieved a high reaction rate and a course of reaction of zeroth order, which is a prerequisite for a truly practical turbidimetric kinetic determination of activity.

By alteration of the quantitative composition within the above-given ranges of variation for the individual components of the reagent, a definite droplet size of the reconstituted emulsion can be obtained which is independent of the method of production. Since the initial extinction of the reagent batch is due to the content of triglyceride, as a rule, one starts from a definite desired triglyceride concentration and the amounts of the other components can then be adapted to the particular requirements with regard to the desired droplet size.

The triglycerides used can be a natural or a synthetic triglyceride with fatty acid residues containing from about 4 to about 22 carbon atoms. Thus, for example, tributyrin has proved to be useful. However, it is preferred to use triglycerides with comparatively long-chained unsaturated fatty acid residues and especially triglycerides with fatty acid residues containing 8 to 20 carbon atoms and 1 to 8 and preferably 1 to 3 carbon-carbon double bonds. Because of its ready availability, triolein is especially preferred but olive oil can also be used. The preferred amount of triglyceride is 0.2 to 2.0% by weight.

The protective colloids used can be those known for this purpose, for example, polyhydroxy compounds, serum albumin, polyvinylpyrrolidone, solid polyethylene oxides and the like. Polyhydroxy compounds are preferred and especially monomeric or polymeric pentoses or hexoses containing up to 10 pentose or hexose units in the molecule and/or polyethylene glycols which are solid at ambient temperature. Preferred examples of polyhydroxy compounds include mannitol and similar sugar alcohols, oligosaccharides derived from glucose, mannose or maltoheptaose, polyethylene glycol with an average molecular weight of from 3500 to 7000 and the like. Other protective colloids which can be used include, for example, amino acids, such as alanine, vegetable gums, such as gum arabic and the like. The preferred amount of protective colloid or of a mixture of protective colloids is 50 to 70% by weight. A mixture of sugar alcohol and polyalkylene glycol has proved to be especially useful.

The bile acids used can be the known surface-active bile acids, such as cholic acid, taurocholic acid, desoxycholic acid, taurodesoxycholic acid, glycodesoxycholic acid or the alkali metal salts thereof, especially the sodium salts. The preferred amount thereof is 10 to 15% by weight.

A further important component of the reagent according to the present invention is colipase, a colipase free from impurities being especially suitable. The preferred amount is 0.003 to 0.01% by weight.

The preserving agent used according to the present invention is one which does not impair the enzymatic activity of the lipase to be determined. Preferred preserving agents include the alkali metal azides and especially sodium azide. However, other preserving agents, for example thiozide and other sulphur-containing preserving agents can also be used. The preferred amount of preserving agent is 0.2 to 0.7% by weight.

Furthermore, the reagent according to the present invention also contains urea, preferably in an amount of from 10 to 15% by weight.

The buffer substances used can be all known buffers which are able to provide a pH value of from 6.0 to 10.5 in the reagent according to the present invention, the preferred pH range being from 8.3 to 9.5. Examples of buffers which can be used include diethanolamine buffer, triethanolamine buffer, tris buffer and Good buffers, such as hepes buffer (very suitable for addition prior to lyophilisation), taps buffer and bicine. Tris buffer is especially preferred. The preferred amount of buffer is from 3 to 10% by weight.

Finally, the reagent according to the present invention also contains an activator for lipase. Lipase activators are known. Preferred activators are chlorides, especially sodium chloride, but other alkali metal and alkaline earth metal chlorides, such as calcium chloride or magnesium chloride, can also be used insofar as they do not lead to the formation of insoluble compounds with other components of the reagent according to the invention or of the sample. Magnesium and calcium ions also have an activating action. However, since calcium ions form insoluble compounds with desoxycholic acid, when calcium is present in the reagent, it is preferable to use taurodesoxycholic acid as bile acid since this permits the presence of higher calcium concentrations in the range of 1 to 5 mMol.

Apart from the above-mentioned essential components, the reagent according to the present invention can, for certain purposes, also contain inert additives (filling materials) which simplify handling.

The manner of working of the individual components of the reagent according to the present invention is not clear in every respect. However, it is assumed that the colipase removes an inhibition of the enzyme brought about by the high content of bile acid salts, especially of desoxycholate, taurodesoxycholate or glycodesoxycholate, and improves the linearity of the course of the reaction. Urea appears to exert an influence on the water/lipid surface of the emulsion and to stabilise it.

The dry reagent according to the present invention can be produced by lyophilisation of an emulsion of the components produced by conventional methods. Buffer substance, urea and possibly also a part of the protective colloid and the preserving agent, as well as possibly of the activator, are preferably added to the "dry emulsion" after lyophilisation. The emulsion subjected to lyophilisation can be produced by conventional methods, for example, by introducing all of the components into an aqueous solvent, emulsifying by conventional methods, such as ultrasonic waves, colloid mills and the like, and subsequently freezing at about −40° C. and drying in a vacuum under conventional conditions, i.e. at about $10^{-1}$ to $10^{-4}$ mm.Hg.

In the case of the lyophilisation, the bile acid salt, colipase, at least 20% by weight of protective colloid, at least a part of the preserving agent and possibly activator must be added. According to a preferred process for the production of an aqueous emulsion intended for lyophilisation, the mentioned components, excluding the triglyceride, are dissolved in water and then, while stirring, a solution of the triglyceride in a volatile organic solvent is injected in a fine stream into the aqueous solution. The volatile organic solvent used can, in particular, be an aliphatic alcohol or a ketone containing up to 4 carbon atoms.

The remaining components of the reagent according to the present invention, namely, buffer substance, urea, and possibly further protective colloid, preserving agent and activator, can be added to the lyophilisate immediately after the production thereof or some time thereafter.

As already mentioned, we have, surprisingly, found that the reagent according to the present invention, after reconstitution, gives an extinction or an extinction change per unit time which is substantially independent of the extinction of the initial emulsion and of the method used for the production of the reagent. Furthermore, the extinction constancy of the reconstituted emulsion is surprisingly good.

The bile acid salts used are preferably freed from impurities, such as decomposition products and the like, for example, by extraction with n-butanol under alkaline conditions, recrystallisation from alcohol/acetone and similar methods of purification.

This surprising property of the reagent according to the invention was investigated by determination of the droplet size distribution before and after lyophilisation with the help of a Coulter counter: this device makes it possible to determine the percentage distribution of the particles of a diameter of from 480 to 16,000 nm in 100 to 1000 nm distances. We found that the droplet distribution before lyophilisation varied very considerably from one batch to another but after the lyophilisation and possibly further process steps, such as admixing other components of the reagents and the like, always displayed a good agreement of the distribution pattern (adjustment of a thermodynamic equilibrium). The dry emulsion thus produced, even when subjected to thermal stress (3 weeks at 35° C.), ensured a very good constancy of droplet distribution. The maximum droplet distribution was found at 500 to 1000 nm. Therefore, the reagent is especially suitable for photometric determination of the clarification of turbidity at 340 to 365 nm. When the droplet size is considerably below 340 nm, decomposition of the triglyceride droplets can no longer be ascertained, whereas large droplets are not an ideal substrate for lipase.

An important advantage of the reagent according to the present invention is that it displays the same activity change per unit time not only in the case of human pancreatic lipase but also in the case of pig pancreatic lipase. Since, in the case of Rick's titrimetric test, both lipases also show the same activity concentration, it is possible to use a pig pancreas-containing standard for calibration.

A further important advantage of the reagent according to the present invention is the absence of a lag phase. It is known that, in the case of the turbidimetric lipase test, only after some time does a reaction course of zeroth order occur. However, such a course of reaction is absolutely necessary for the exact determination of the activity concentration of an enzyme (cf. H. U. Bergmeyer, Grundlagen der enzymatischen Analyse, 1979, p.58 et seq.). The time up to the achievement of this course of reaction is called the lag phase.

BRIEF DESCRIPTION OF DRAWINGS

FIG. 4 shows droplet size distribution, stressed and unstressed, with reference to Example 9 herein.

Figure 1:
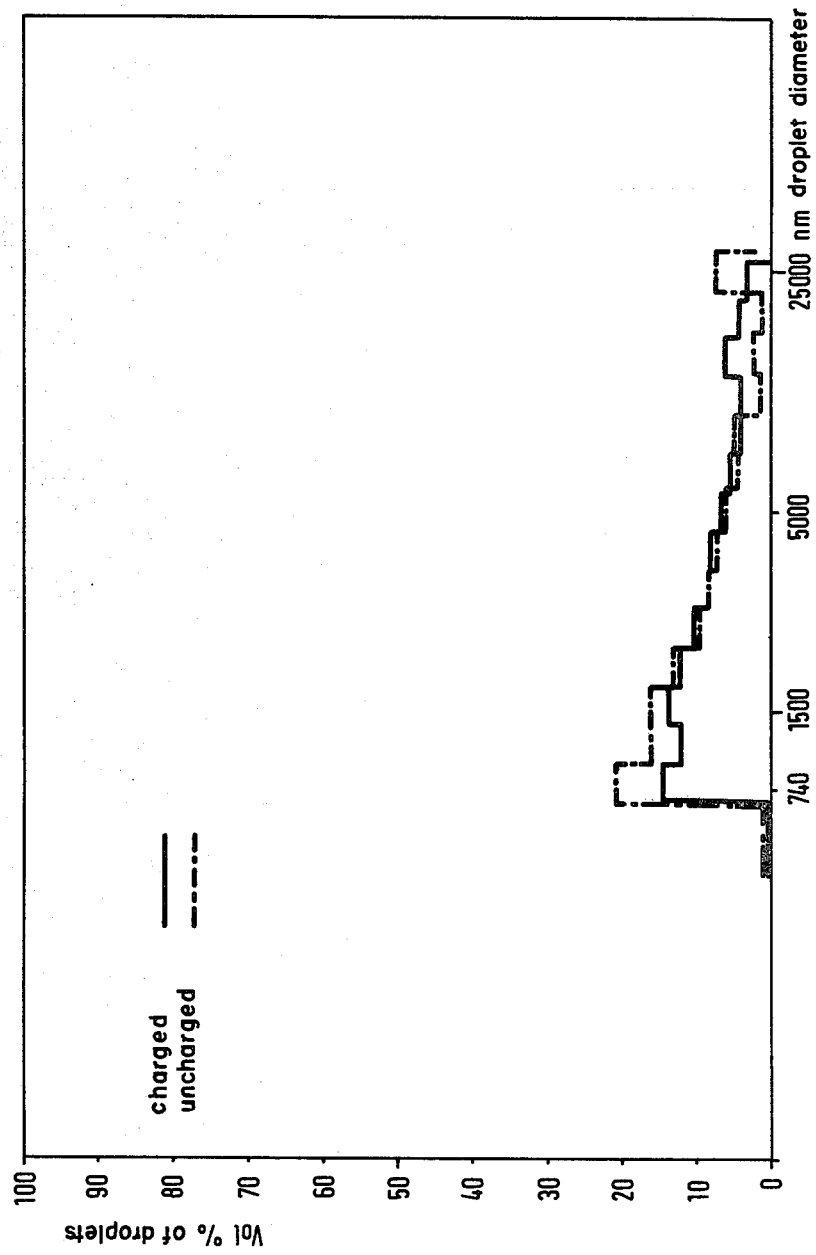
FIG. 1 shows the distribution of particle size after reconstitution, not only in freshly prepared state, but also after 3 weeks stressing at 35° C. in a dry state, with reference to Example 2 herein.

The following Examples are given for the purpose of illustrating the present invention, reference thereby also being made to the accompanying drawings, which show graphically the droplet size distributions of the emulsions obtained with a Coulter counter in the various Examples and described experiments.

EXAMPLE 1

0.06 g. Calcium chloride, 22.72 g. sodium desoxycholate, 25.35 g. polyethylene glycol (M.W. 4000), 1.1 g. sodium azide, 0.02 g. colipase and 50.8 parts by weight mannitol are dissolved in 1.0 liter distilled water. Into the solution obtained is injected, with stirring, 1.42 g. triolein, dissolved in 32 ml. n-propanol, at a pressure of 2 bar, through a nozzle of 1.5 mm. diameter. The triolein emulsion so obtained is frozen at $-40°$ C. and dried by lyophilisation.

8.95 g. Sodium desoxycholate, 7.25 g. tris, 1.20 g. tris hydrochloride, 7.5 g. polyethylene glycol (M.W. 4000), 1.97 g. sodium chloride, 16.2 g. urea and 56.9 g. mannitol are mixed together in dry form. 2 Parts by weight of the buffer mixture so obtained are mixed with 1 part by weight of the lyophilisate, using a spiral mixer, to give a homogeneous reagent.

For carrying out a lipase determination, 150 mg. of this reagent are taken up in 2.5 ml. water, mixed with 0.1 ml. of sample and measured photometrically at 365 nm and at 25° C. The samples used can be, for example, serum, duodenal juice, urine and other body fluids.

The correctness of the method was ascertained by comparison with Rick's titrimetric method. In the case of an investigation of 60 human sera with various lipase activities, the following data were obtained: correlation: (x=Rick; y=test according to the present invention) y=0.93·x−20; r=0.96.

The linearity of the test was maintained up to about 1300 Rick units/1.

One Rick unit=1 µmol LFA/minute=1U
LFA=liberated fatty acids.

EXAMPLE 2

1.5 g. Mannitol, 0.900 g. polyethylene glycol (M.W. 4000), 0.524 g. sodium desoxycholate, 1.5 mg. colipase and 8 mg. sodium azide are dissolved in 50 ml. distilled water. Into this solution are injected, through a fine nozzle, 150 mg. triolein dissolved in 5.0 ml. n-propanol, with stirring. The emulsion obtained is frozen at $-40°$ C. and lyophilised.

3.50 g. Urea, 3.73 g. sodium desoxycholate, 0.4 g. sodium chloride, 0.10 g. sodium azide, 2 mg. calcium chloride, 1.355 g. tris and 0.200 g. tris hydrochloride are intimately mixed together. To this mixture is added the comminuted dry lyophilisate and homogeneously mixed.

The complete mixture of 12.3705 g. weight contains:

| | | |
|---|---|---|
| mannitol | 1.500 g. | total = 2.4 g. |
| polyethylene glycol | 0.900 g., | = 19.4% by wt. |
| sodium desoxycholate | 4.254 g. | = 34.4% by wt. |
| colipase | 1.5 mg. | 0.01% by wt. |
| triolein | 0.150 g. | 1.2% by wt. |
| sodium azide | 0.108 g. | 0.9% by wt. |
| Ca/Nachloride | 0.402 g. | 3.3% by wt. |
| tris | 1.355 g. | total = 1.555 g. |
| tris hydrochloride | 0.200 g. | = 12.6% by wt. |
| urea | 3.5 g. | = 28.3% by wt. |

37 mg. of this mixture are dissolved in 2.5 ml. distilled water and measured photometrically with 200 µl. sample (serum) at 340 nm and at 25° C. or 30° C. against water or air. The lipase activity is determined from the extinction difference/minute.

The distribution of the particle size after reconstitution, not only in a freshly prepared state but also after 3 weeks stressing at 35° C. in a dry state, measured on a Coulter counter, is shown in FIG. 1 of the accompanying drawings.

EXAMPLE 3

8.41 g. Bovine serum albumen, 12.2 g. sodium desoxycholate, 0.02 g. sodium azide and 0.034 g. colipase are dissolved in 100 ml. distilled water. While stirring, a solution of 3.5 g. triolein in 7 ml. n-propanol is injected into this solution under pressure. The emulsion thus obtained is frozen at $-40°$ C. and lyophilised.

17.4 g. Mannitol, 4 g. solid polyethylene glycol, 7 g. urea, 7.47 g. sodium desoxycholate, 0.82 g. sodium chloride, 0.2 g. sodium azide, 2.71 g. tris and 0.4 g. tris hydrochloride are ground and intimately mixed together. The comminuted dry emulsion is added thereto and homogeneously mixed.

90 mg. of this powdered reagent are added to 2 ml. distilled water and, after dissolving, mixed with 100 µl. of sample (serum). The reaction is followed photometrically at 340 (365) nm Hg.

EXAMPLE 4

8.41 g. Alanine, 1.22 g. sodium desoxycholate, 0.02 g. sodium azide and 0.034 g. colipase are dissolved in 100 ml. distilled water. While stirring, a solution of 3.5 g. triolein in 7 ml. n-propanol is injected under pressure into this solution. The emulsion thus obtained is frozen at −40° C. and lyophilised.

17.4 g. Mannitol, 4 g. solid polyethylene glycol, 7 g. urea, 7.47 g. sodium desoxycholate, 0.82 g. sodium chloride, 0.2 g. sodium azide, 2.71 g. tris and 0.4 g. tris hydrochloride are ground and intimately mixed together. The comminuted dry emulsion is added thereto and homogeneously mixed.

90 mg. of the powdered reagent are added to 2 ml. distilled water and, after dissolving, mixed with 100 μl. of sample (serum). The reaction is followed photometrically at 340 (365) nm.

EXAMPLE 5

4.205 g. Polyethylene glycol (M.W. 4000), 4.205 g. bovine serum albumen, 1.22 g. sodium desoxycholate, 0.02 g. sodium azide and 0.034 g. colipase are dissolved in 100 ml. distilled water. While stirring, a solution of 3.5 g. triolein in 7 ml. n-propanol is injected into this solution under pressure. The emulsion thus obtained is frozen at −40° C. and lyophilised.

17.4 g. Mannitol, 4 g. polyethylene glycol (M.W. 4000), 7 g. urea, 7.47 g. sodium desoxycholate, 0.82 g. sodium chloride, 0.2 g. sodium azide, 2.71 g. tris and 0.4 g. tris hydrochloride are ground and intimately mixed together. The comminuted dry emulsion is added thereto and homogeneously mixed.

90 mg. of this powdered reagent are added to 2 ml. distilled water and, after dissolving, mixed with 100 μl. of sample (serum). The reaction is followed photometrically at 340 (365) nm Hg.

EXAMPLE 6

6.73 g. Polyethylene glycol (Polywax 4000), 1.68 g. polyvinylpyrrolidone, 1.22 g. sodium desoxycholate, 0.02 g. sodium azide and 0.034 g. colipase are dissolved in 100 ml. distilled water. While stirring, a solution of 3.5 g. triolein in 7 ml. n-propanol is injected under pressure into this solution. The emulsion thus obtained is frozen at −40° C. and lyophilised.

17.4 g. Mannitol, 4 g. polyethylene glycol, 7 g. urea, 7.47 g. sodium desoxycholate, 0.82 g. sodium chloride, 0.2 g. sodium azide, 2.71 g. tris and 0.4 g. tris hydrochloride are ground and intimately mixed together. The comminuted dry emulsion is added thereto and homogeneously mixed.

90 mg. of this powdered reagent are added to 2 ml. distilled water and, after dissolving, mixed with 100 μl. of sample (serum). The reaction is followed photometrically at 340 (365) nm Hg.

EXAMPLE 7

(Comparative Example with insufficient bile acid added)

4.69 g. Mannitol, 4.69 g. polyethylene glycol (Polywax 4000), 0.38 g. sodium desoxycholate, 0.02 g. sodium azide and 0.034 g. colipase are dissolved in 100 ml. distilled water. While stirring, a solution of 3.5 g. triolein in 7 ml. n-propanol is injected under pressure into this solution. The emulsion thus obtained is frozen at −40° C. and lyophilised.

17.4 g. Mannitol, 4 g. polyethylene glycol (M.W. 4000), 7 g urea, 7.47 g. sodium desoxycholate, 0.82 g. sodium chloride, 0.2 g. sodium azide, 2.71 g. tris and 0.4 g. tris hydrochloride are ground and intimately mixed together. The comminuted dry emulsion is added thereto and homogeneously mixed.

90 mg. of the powdered reagent are added to 2 ml. distilled water and, after dissolving, mixed with 100 μl. of sample (serum). The reaction is followed photometrically at 340 (365) nm Hg.

Figure 2:
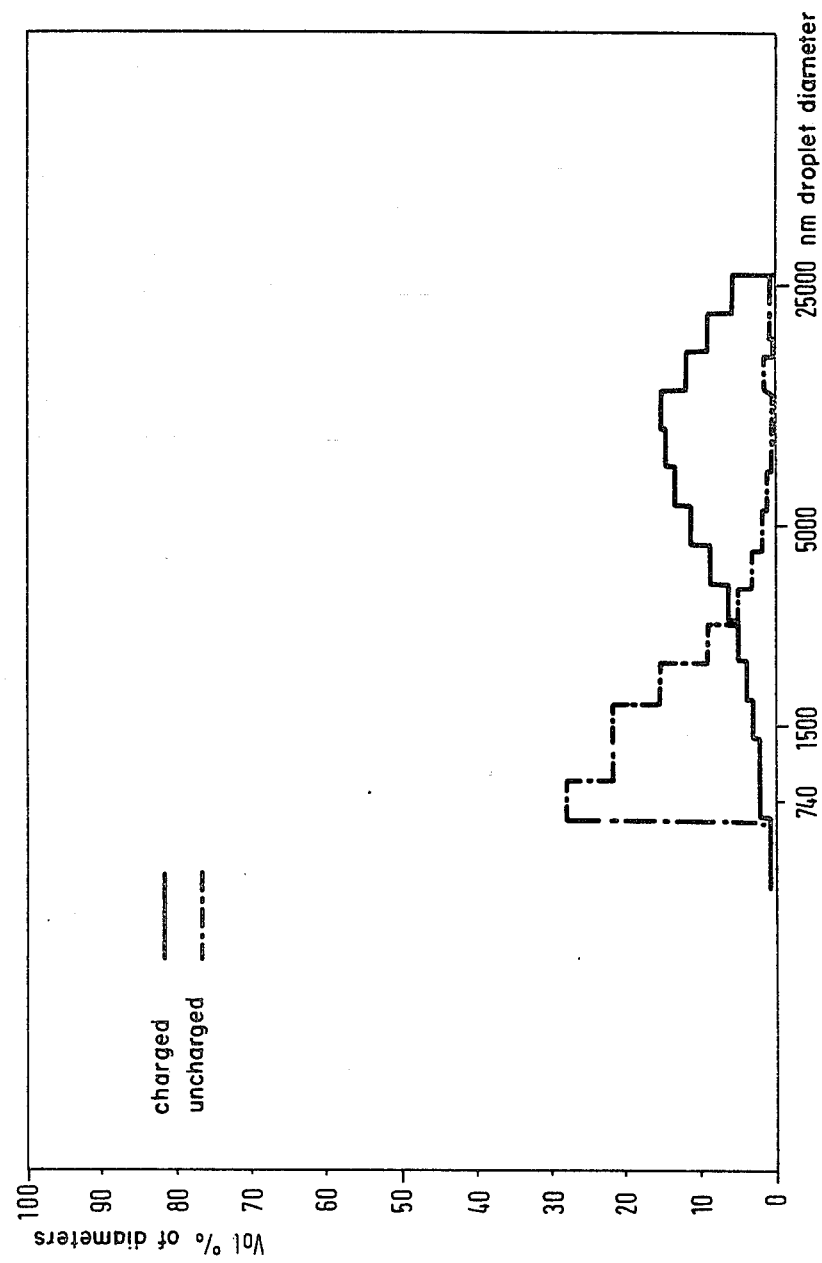
FIG. 2 shows distribution of particle size, with and without stressing, with reference to Example 7 herein.

The distribution of the particle size, with and without stressing (see Example 2), is shown in FIG. 2 of the accompanying drawings.

EXAMPLE 8

(Comparative Example)

3.76 g. Mannitol, 5.63 g. polyethylene glycol (M.W. 4000), 0.19 g. sodium desoxycholate, 0.02 g. sodium azide and 0.034 g. colipase are dissolved in 100 ml. distilled water. While stirring, a solution of 3.5 g. triolein in 7 ml. n-propanol is injected under pressure into this solution. The emulsion thus obtained is frozen at −40° C. and lyophilised.

17.4 g. Mannitol, 4 g. polyethylene glycol (M.W. 4000), 7 g. urea, 7.47 g. sodium desoxycholate, 0.82 g. sodium chloride, 0.2 g. sodium azide, 2.71 g. tris and 0.4 g. tris hydrochloride are ground and intimately mixed together. The comminuted dry emulsion is added thereto and homogeneously mixed.

90 mg. of this powdered reagent are added to 2 ml. distilled water and, after dissolving, mixed with 100 μl. of sample (serum). The reaction is followed photometrically at 340 (365) nm Hg.

Figure 3:
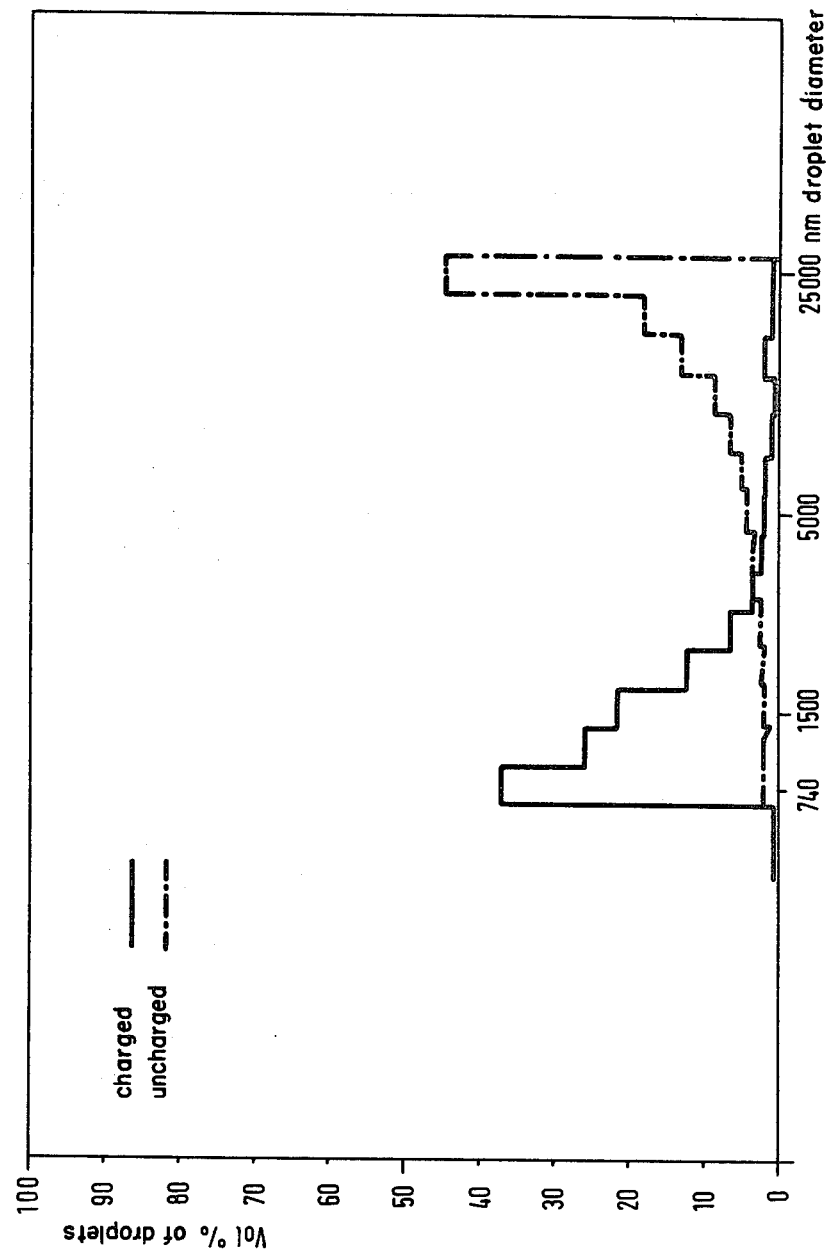
FIG. 3 shows distribution of particle size, with and without stressing, with reference to Example 8 herein.

The distribution of the particle size, with and without stressing (see Example 2), is shown in FIG. 3 of the accompanying drawings.

EXAMPLE 9

8.88 g. Mannitol, 0.86 g. sodium desoxycholate, 0.1 g. sodium azide and 0.034 g. colipase are dissolved in 100 ml. distilled water. While stirring, a solution of 2.5 g. triolein in 7 ml. n-propanol is injected under pressure into this solution. The emulsion thus obtained is frozen at −40° C. and lyophilised.

22.4 g. Mannitol, 4 g. polyethylene glycol (M.W. 4000), 2 g. urea, 7.47 g. sodium desoxycholate, 0.82 g. sodium chloride, 0.2 g. sodium azide, 2.71 g. tris and 0.4 g. tris hydrochloride are ground and intimately mixed together. The comminuted dry emulsion is added thereto and homogeneously mixed.

90 mg. of this powdered reagent are added to 2 ml. distilled water and, after dissolving, mixed with 100 μl. of sample (serum). The reaction is followed photometrically at 340 (365) nm Hg.

The droplet size distribution, stressed and non-stressed (cf. Example 2), is shown in FIG. 4 of the accompanying drawings.

EXAMPLE 10

In 1000 ml. distilled water are dissolved 75 g. mannitol, 25 g. polyethylene glycol (M.W. 4000), 20 g. sodium taurodesoxycholate, 55 mMol HEPES buffer (pH 6.8), 0.3 g. calcium chloride and 9 mg. colipase. Into this solution is injected, with stirring, a solution of 1 g. triolein and 1 ml. amounts of this emulsion are placed into ampoules and lyophilised.

The lyophilisate is dissolved in 2.0 ml. distilled water. The lipase determination is carried out by adding 100 μl. of serum and measuring photometrically at 340 or 365 nm.

When this lyophilisate is stored at 4° C. and at 35° C. for 3 weeks and then dissolved in double distilled water, no difference is ascertained in the initial extinction and in the course of the test.

(HEPES = 2-[4-(2-hydroxyethyl)-piperazine-(1)]-ethanesulphonic acid).

It will be understood that the specification and examples are illustrative but not limitative to the present invention and that other embodiments within the spirit and scope of the invention will suggest themselves to those skilled in the art.

We claim:

1. A reconstitutable dry reagent for the turbidimetric determination of lipase, which reagent forms an emulsion upon adding water and comprises substrate oil, protective colloid, emulsifier and an activator for lipase, said reagent containing:
   0.2 to 10% by weight of liquid triglyceride,
   20 to 90% by weight of protective colloid,
   5 to 60% by weight of an alkali metal salt of bile acid,
   0.001 to 0.1% by weight of colipase,
   0.1 to 2.0% by weight of preserving agent,
   5 to 20% by weight of urea,
   3 to 50% by weight of buffer substance for pH 6.0 to 10.5 and
   0.5 to 5% by weight of said activator.

2. A reagent as claimed in claim 1 wherein the fatty acid residues of the triglyceride each contain 8 to 20 carbon atoms and 1 to 8 carbon-carbon double bonds.

3. A reagent as claimed in claim 1 containing 0.2 to 2.0% by weight of triglyceride.

4. A reagent as claimed in claim 1 wherein the protective colloid is one or more polyhydroxy compounds.

5. A reagent as claimed in claim 4 wherein the polyhydroxy compound is a monomeric or polymeric pentose or hexose containing up to 10 pentose to hexose units in the molecule.

6. A reagent as claimed in claim 5 wherein the polyhydroxy compound is a solid polyethylene glycol.

7. A reagent as claimed in claim 1 containing 50 to 70% by weight of protective colloid.

8. A reagent as claimed in claim 1 containing 10 to 15% by weight of bile acid salt.

9. A reagent as claimed in claim 1 containing 0.003 to 0.01% by weight of colipase.

10. A reagent as claimed in claim 1 wherein the preserving agent is an alkali metal azide.

11. A reagent as claimed in claim 1 containing 10 to 15% by weight of urea.

12. A reagent as claimed in claim 1 containing 3 to 10% by weight of buffer substance.

13. A reagent as claimed in claim 1 wherein the buffer substance is hepes buffer, tabs buffer, Good buffer, tris buffer, triethanolamine buffer or diethanolamine buffer.

14. A reagent as claimed in claim 1 wherein the activator is sodium, calcium or magnesium chloride.

15. Process for the preparation of a dry reagent as claimed in claim 1 which process comprises preparing an aqueous emulsion of a triglyceride containing bile acid salt, colipase, at least 10% by weight of protective colloid, and at least a part of a preserving agent, lyophilizing the emulsion, mixing the lyophilizate with a buffer substance and urea and recovering said dry reagent.

16. Process as claimed in claim 15 wherein said aqueous emulsion also contains an activator.

17. Process as claimed in claim 15 wherein the said lyophilizate is mixed with a buffer and urea and additionally at least one of a protective colloid, a preserving agent and an activator.

18. Process as claimed in claim 15 wherein, into a solution of protective colloid, bile acid salt, colipase and optionally preserving agent and activator, there is injected in a fine stream, while stirring, a solution of the triglyceride in a volatile organic solvent.

* * * * *